US00PP25848P3

(12) United States Plant Patent
Bradford et al.

(10) Patent No.: US PP25,848 P3
(45) Date of Patent: Sep. 1, 2015

(54) NECTARINE TREE NAMED 'SIERRA PEARL'

(50) Latin Name: *Prunus persica*
Varietal Denomination: Sierra Pearl

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 105 days.

(21) Appl. No.: 13/998,859

(22) Filed: Dec. 16, 2013

(65) Prior Publication Data

US 2015/0173274 P1 Jun. 18, 2015

(51) Int. Cl.
*A01H 5/08* (2006.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

PP6,363 P 11/1988 Bradford et al.
PP10,926 P 6/1999 Bradford et al.

*Primary Examiner* — Susan McCormick Ewoldt

(57) ABSTRACT

The present invention relates to a new and distinct variety of nectarine tree, *Prunus persica,* broadly characterized by a medium size, vigorous, hardy, self-fertile, productive and regular bearing tree. The variety blooms during the mid season and requires about 550 chilling hours. The fruit matures under the ecological conditions described in late July, with first picking on Jul. 26, 2013. The fruit is medium in size, globose in shape, clingstone in type, firm in texture, white in flesh color, mostly red in skin color, and a tasty blend of acid and high sugar.

1 Drawing Sheet

Botanical classification: *Prunus persica.*
Variety denomination: 'Sierra Pearl'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Sierra Pearl'.

The present variety was hybridized by us in 2004 as a first generation cross using 'August Red' (U.S. Plant Pat. No. 6,363) nectarine as the selected seed parent and an unnamed clingstone peach as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of our experimental orchard located near Le Grand, Calif., in Merced County (San Joaquin Valley). During the fruit evaluation season of 2008 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'August Red' (U.S. Plant Pat. No. 6,363) nectarine by producing nectarines that are medium size, firm, mostly red in skin color, globose in shape, clingstone in type, but is quite distinguished therefrom by producing fruit that is white in flesh color instead of yellow and that matures about twenty days earlier.

The present variety is most similar to 'August Pearl' (U.S. Plant Pat. No. 10,926) nectarine by being self-fruitful, by having globose leaf glands, and by producing nectarines that are similar in size, firm in texture, mostly red in skin color, white in flesh color, globose in shape, clingstone in type and excellent in flavor, but is distinguished therefrom by producing fruit that matures about one week earlier and that has a bitter kernel instead of sweet.

SUMMARY OF VARIETY

In summary, the present nectarine variety is characterized by a medium size, vigorous, hardy, self-fertile, productive and regular bearing tree. The variety blooms during the mid season and requires about 550 chilling hours. The fruit matures under the ecological conditions described in late July, with first picking on Jul. 26, 2013. The fruit is medium in size, globose in shape, clingstone in type, firm in texture, white in flesh color, mostly red in skin color, and a tasty blend of acid and high sugar.

DRAWING

The accompanying photograph consists of four whole fruits positioned to display the characteristics of the skin color and form, one sliced fruit to reveal the flesh and stone, two insets to reveal buds and blossoms, characteristic leaves, and a tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 29, 2013, on a five year old tree multiplied from the original. The blossom and flower descriptions were made the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'August Red' (U.S. Plant Pat. No. 6,363) nectarine.

Pollen parent: Unnamed yellow flesh peach.

TREE

Size: Medium, reaching and maintaining a height of 7' [2.13 m.] and a spread of 8' [2.44 m.] after five growing seasons utilizing typical dormant pruning.

Vigor: Vigorous, responding typically to irrigation and fertilization. The variety grows about 2' [0.61 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 550 hours.

Trunk:

- *Size.*—Medium slender, reaching a maximum diameter of 2¾" [69.9 mm.] after the fifth growing season.
- *Texture.*—Medium smooth.
- *Bark color.*—A Light grayish brown [60. l.gy.Br] and Brownish grayish [64. brGy] variegation.
- *Lenticels.*—Approximate Number Per Square Inch: 12. Color: Strong brown [55. s.Br]. Average Size: ⅛" [3.2 mm.]. Shape: Eye-shaped, elongated.

Branches:

- *Size.*—Diameter of main scaffold is 2¼" [57.2 mm.] measured 12" above crotch. Diameter of limb is 1½" [38.1 mm.] measured 12" above first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. Older Wood: Moderate yellowish brown [77. m.yBr] with Strong yellowish brown [74. s.yBr] variegation.
- *Lenticels.*—Number Per Square Inch: About 60 on second year wood. Color: Light yellowish brown [76. l.yBr]. Average size: 1/64" [0.4 mm.] to 1/16" [1.6 mm.] on second year wood. Shape: Rectangular, elongated.

Leaves:

- *Size.*—Large. Average Length: 5½" [139.7 mm.]. Average Width: 1⅝" [41.3 mm.].
- *Arrangement.*—Alternate.
- *Thickness.*—Medium.
- *Form.*—Elliptical.
- *Apex.*—Acuminate.
- *Base.*—Acute, with an average base angle of 65 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Pale yellow green [121. p.YG].
- *Petiole.*—Average Length: ⅜" [9.5 mm.]. Average Thickness: 1/16" [1.6 mm.]. Color: Light yellow green [119. l.YG].
- *Stipules.*—Number: Usually 2 per leaf, up to 6 per growing tip. Average Length: ¼" [6.4 mm.]. Color: Brilliant yellow green [116. brill.YG] becoming Dark olive green [126. d.OlG] with maturity.
- *Glands.*—Number: 2 to 4 per leaf. Position: Slightly alternate, almost always in pairs, positioned on petiole and base of blade. Size: Small. Form: Globose. Color: Dark olive green [126. d.OlG] becoming Moderate olive green [125. m.OlG] with age.
- *Leaf buds.*—Pointed, medium in size.

Flower buds:

- *Hardiness.*—Hardy, with respect to central California winters.
- *Diameter.*—Typically 5/16" [7.9 mm.] 1 week before bloom.
- *Length.*—Typically ⅝" [15.9 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, about thirty stamens, five sepal and petal locations alternately positioned.

- *Type.*—Showy, large.
- *Average flower diameter.*—2" [50.8 mm.].
- *Number of petals.*—Usually five, extra petal fragments commonly occur, double blossoms rarely observed.
- *Petal shape.*—Circular to oval.
- *Petal margin.*—Entire, somewhat wavy, occasional notches.
- *Average petal diameter.*—13/16" [20.6 mm.].
- *Average petal length.*—13/16" [20.6 mm.].
- *Petal apex.*—Rounded.
- *Petal base.*—Rounded to somewhat truncate.
- *Petal color.*—Pale pink [7. p.Pk] toward the apex, Light purplish pink [249. l.pPk] toward the base on both sides.

*Anther color.*—Light orange [52. l.O] over a Light yellow [86. l.Y] center at bloom onset.
*Stigma Color.*—Light greenish yellow [101. l.gY].
*Average pistil length.*—¾" [19.1 mm.].
*Average stamen length.*—⅝" [15.9 mm.].
*Sepal color.*—Dark purplish red [259. d.pR] on the outer surface.
*Sepal length.*—¼" [6.4 mm.].
*Sepal width.*—3/16" [4.8 mm.].
*Sepal apex.*—Rounded to elliptical to match the sepal length and width.
*Fragrance.*—Moderate.
*Blooming period.*—Medium, 2 days after 'Spring Bright' (U.S. Plant Pat. No. 7,507) nectarine.
*Onset of bloom.*—One percent on Mar. 6, 2013.
*Date of full bloom.*—Mar. 14, 2012.
*Duration of bloom.*—One to two weeks, dependent on ambient temperature.
*Number per cluster.*—1 to 3 with single flowers most common.

FRUIT

Maturity when described: Firm ripe, Jul. 29, 2013.
Date of first picking: Jul. 26, 2013.
Date of last picking: Aug. 10, 2013.
Size: Medium.
*Average diameter axially.*—2⅞" [73 mm.].
*Average diameter across suture plane.*—2¾" [69.9 mm.].
*Average diameter across cheek plane.*—2¾" [69.9 mm.].
*Typical weight.*—7.4 ounces [210 grams].
Form: Globose, slightly asymmetrical.
*Longitudinal section form.*—Fairly oblate.
*Axial view.*—Round.
Suture: Extends from the base, along the side, and just past the pistil point.
*Near the base.*—A medium groove.
*Along the side.*—A shallow trough.
*Near the apex.*—A shallow groove.
Ventral surface: Rounded, lipped throughout on both sides.
Lips: Unequal.
Cavity: Flaring, elongated in suture plane, suture showing on one side, Pale yellow green [121. p.YG] stem markings typical.
*Depth.*—½" [12.7 mm.].
*Breadth.*—⅞" [22.2 mm.].
Base: Rounded to oblate.
Apex: Truncate, but somewhat cordate if viewed parallel to the suture.
Pistil point: Apical, very short, usually depressed within the suture.
Stem: Medium.
*Average length.*—5/16" [7.9 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed in dry season.
*Color.*—Dark red [16. d.R] over a Light yellowish pink [28. l.yPk] background with Pale yellow green [121. p.YG] freckling throughout.
Flesh:
*Color.*—Yellowish white [92. yWhite] with some Deep red [13. deep R] streaking toward the stone.
*Surface of pit cavity.*—Covered with Deep red [13. deep R] broken fibers when twisted from the stone.
*Amygdalin.*—Scarce.
*Juice.*—Moderate, rich.
*Texture.*—Firm, tough, meaty.
*Fibers.*—Few, coarse, tough.
*Ripens.*—Earlier at the apex.
*Flavor.*—A tasty blend of sugar and acid, typically 19 brix.
*Aroma.*—Very slight.
*Eating quality.*—Excellent.

STONE

Type: Clingstone.
Form: Oval.
Hilum: Narrow, oval.
Base: Slightly rounded to flat.
Apex: Acute to acuminate.
Sides: Unequal.
Surface: Irregularly furrowed toward the apex, pitted toward the base.
Ridges: Rounded, more toward the apex.
External color: Moderate reddish brown [43. m.rBr].
Pit wall color when cracked: Moderate yellowish brown [77. m.yBr].
Cavity surface color: Strong yellowish brown [74. s.yBr].
Average pit wall thickness: ¼" [6.4 mm.].
Average width: 1" [25.4 mm.].
Average length: 1 7/16" [36.5 mm.].
Average breadth: ¾" [19.1 mm.].
Tendency to split: None observed.
Kernel:
*Form.*—Oval.
*Skin color.*—Light orange yellow [70. l.OY] when dry.
*Pellicle color.*—Strong yellowish brown [74. s.yBr].
*Vein color.*—Brilliant orange yellow [67. brill.OY].
*Taste.*—Bitter.
*Viable.*—Yes.
*Average width.*—7/16" [11.1 mm.].
*Average length.*—13/16" [20.6 mm.].
*Amygdalin.*—Scant.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'August Pearl' (U.S. Plant Pat. No. 10,926) nectarine by being self-fruitful, by having globose leaf glands, and by producing nectarines that are similar in size, firm in texture, mostly red in skin color, white in flesh color, globose in shape, clingstone in type and excellent in flavor, but is distinguished therefrom by producing fruit that matures about one week earlier and that has a bitter kernel instead of sweet.

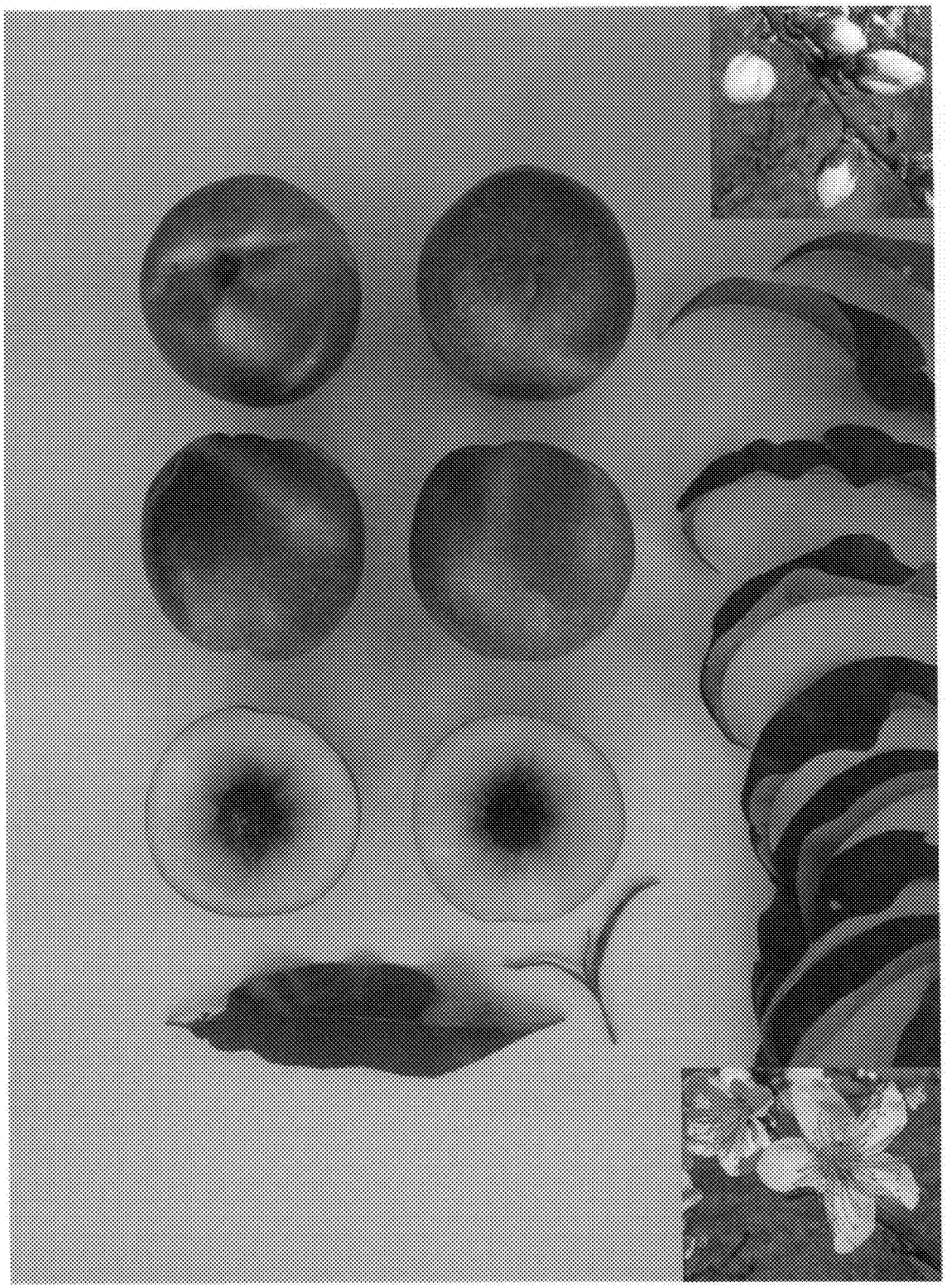

* * * * *